United States Patent [19]

Ochsner

[11] 4,066,710

[45] Jan. 3, 1978

[54] UNSATURATED ALCOHOL

[75] Inventor: Paul Albert Ochsner, Geneva, Switzerland

[73] Assignee: Givaudan Corporation, Clifton, N.J.

[21] Appl. No.: 715,963

[22] Filed: Aug. 19, 1976

Related U.S. Application Data

[63] Continuation of Ser. No. 430,354, Jan. 2, 1974, abandoned.

[51] Int. Cl.$^2$ ............................................. C07C 33/02
[52] U.S. Cl. ........................ 260/631.5; 260/332.1; 260/614 R; 252/522; 252/89 R; 252/108; 424/65; 424/70; 560/261
[58] Field of Search ............. 260/631.5, 614 R, 488 H

[56] References Cited

U.S. PATENT DOCUMENTS

| 3,075,003 | 1/1963 | Blumenthol | 260/488 H |
|---|---|---|---|
| 3,330,867 | 7/1967 | Saucy | 260/488 H |
| 3,344,171 | 9/1967 | Lemberg | 260/631.5 |

FOREIGN PATENT DOCUMENTS

| 2,363,535 | 11/1974 | Germany | 260/631.5 |
|---|---|---|---|
| 2,463,630 | 8/1974 | Germany | 260/631.5 |

OTHER PUBLICATIONS

Stevens et al., Tetrahedron, vol. 28, pp. 1938-1944 (1972).
Clark et al., Chem. Abst., vol. 84, p. 387, #65175q, (Int. Congr. Essent. Oils, 6th, 1974, 70, 10 pages, (1976).

Primary Examiner—Bernard Helfin
Assistant Examiner—James H. Reamer
Attorney, Agent, or Firm—Thomas Cifelli, Jr.; Robert F. Tavares

[57] ABSTRACT

Novel octadiene odorants, odorant compositions containing same, and process for producing said odorants and compositions.

1 Claim, No Drawings

UNSATURATED ALCOHOL

This is a continuation, of application Ser. No. 430,354 filed Jan. 2, 1974, now abandoned.

FIELD OF THE INVENTION

This invention relates to novel chemicals and fragrance compositions.

SUMMARY OF THE INVENTION

The novel octadiene, olfactory derivatives provided by the present invention have the following general formula

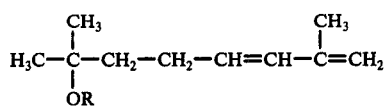

wherein R represents a hydrogen atom or a $C_{1-5}$-alkyl, $C_{2-5}$-alkenyl or $C_{1-5}$-alkanoyl group.

Examples of $C_{1-5}$-alkyl groups are methyl, ethyl, etc.
Examples of $C_{2-5}$-alkenyl groups are allyl, crotyl, etc.
Examples of $C_{1-5}$-alkanoyl groups are acetyl, propionyl, etc.

According to the process provided by the present invention, the octadiene derivatives of formula I are manufactured by hydrating 2,7-dimethyl-1,3,7-octatriene of the formula

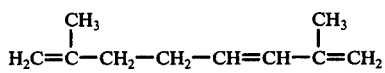

with intermediate protection of the conjugated double-bonds to give 2,7-dimethyl-5,7-octadien-2-ol and, if desired, subjecting said octadien-2-ol to esterification to give an octadiene derivative of formula I in which R represents a $C_{1-5}$-alkanoyl group or to etherification to give an octadiene derivative of formula I in which R represents a $C_{1-5}$-alkyl or $C_{2-5}$-alkenyl group.

The octadiene derivatives of formula I possess particular odorant properties. They can accordingly be used in the perfume industry for the manufacture of perfumes and perfume products; for example, for the perfuming of soaps, solid and liquid detergents, aerosols and cosmetic products of all kinds such as toilet waters, ointments, face milks, make-ups, lipsticks, bath salts and bath oils. In the finished perfumes or perfumed products, the content of the present octadiene derivatives can lie within wide limits; for example, between about 1% (detergents) and about 20% (alcoholic solutions). In perfume bases or concentrates, the octadiene derivatives can, of course, also be present in amounts greater than 20%.

DESCRIPTION OF THE PREFERRED EMBODIMENTS

The aforementioned intermediate protection of the conjugated double-bonds in 2,7-dimethyl-1,3,7-octatriene of formula II can be expediently achieved by converting said octatriene into the sulphone of formula III (see the following formula scheme). Water can then be added according to methods known per se at the terminal double-bond of this sulphone and the resulting hydrated sulphone of formula IV can be finally converted into 2,7-dimethyl-5,7-octadien-2-ol (formula I; R = H) by removal of the protecting group.

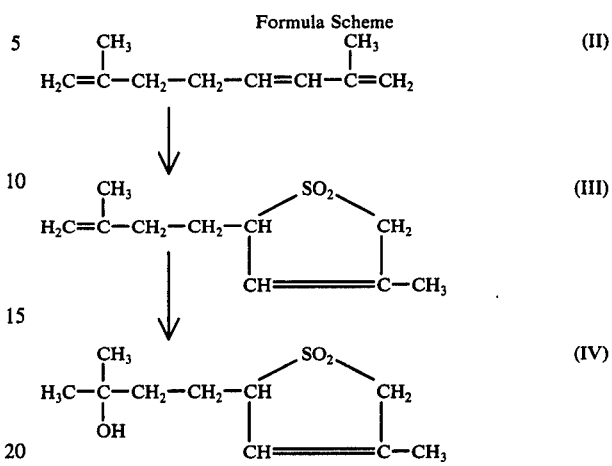

According to the foregoing formula scheme, 2,7-dimethyl-1,3,7-octatriene of formula II is converted into the sulphone of formula III using an excess of sulphur dioxide in the presence of about 1% of a polymerisation inhibitor, for example, hydroquinone, 3-tertbutyl-4-methoxyphenol, 2,6-di(tertbutyl)-4-methylphenol (BHT) etc. After removal of the excess sulphur dioxide, this sulphone of formula III is hydrated at the terminal double-bond; for example, by the action of 40–60% aqueous sulphuric acid, expediently at temperatures of ca 10°–25° C. The resulting product of formula IV is neutralized (e.g., with sodium hydroxide) and separated with a solvent (e.g., benzene).

The removal of the $SO_2$-protecting group and, concommitantly, the re-introduction of the conjugated double-bond can be carried out by heating the compound of formula IV, expediently in a vacuum and at temperatures of ca 120°–130° C.

It has proved to be advantageous to carry out the heating of the compound of formula IV in the presence of ca 1–2% of a high-boiling organic base; for example, triethanolamine or a tertiary amine such as a trialkylamine (e.g., trimethylamine). Inorganic compounds which have a weak basic reaction (e.g., calcium carbonate) can also be used.

The intermediate protection of the conjugated double-bonds can also be achieved by converting 2,7-dimethyl-1,3,7-octatriene of formula II into the iron pentacarbonyl complex by treatment with iron pentacarbonyl (e.g., by heating for several hours in a high-boiling solvent such as dibutyl ether under reflux). The iron pentacarbonyl complex obtained can then be hydrated (e.g., in the presence of a strong acid such as 50–80% sulphuric acid) and the hydrated compound can subsequently be decomposed to give the octadiene derivative of formula I in which R represents a hydrogen atom (see, for example, Belgian Pat. No. 723,127).

The esterification of the resulting alcohol (2,7-dimethyl-5,7-octadien-2-ol) can be carried out according to methods known per se, expediently by reacting the alcohol with a compound yielding the desired $C_{1-5}$-alkanoyl group, especially using an appropriate acid anhydride such as acetic anhydride, in the presence of a base (e.g., pyridine, sodium acetate, etc). A corresponding acid halide can, however, also be used for this esterification.

The etherification of the resulting alcohol (2,7-dimethyl-5,7-octadien-2-ol) can likewise be carried out according to methods known per se for the etherification of alcohols (see, for example, Houben-Weyl, Methoden der organischem Chemie 6/2, page 5 et seq., Georg Thieme Verlag Stuttgart, 1965). It is expedient to convert the 2,7-dimethyl-5,7-octadien-2-ol into an alkali metal salt and to react this salt with a $C_{1-5}$-alkyl or $C_{2-5}$-alkenyl halide or a di($C_{1-5}$-alkyl) or di($C_{2-5}$-alkenyl) sulphate.

Examples of suitable alkali metal salts are the lithium, sodium or potassium salt. The sodium salt and the potassium salt are preferred.

Examples of alkyl or alkenyl halides are the corresponding chlorides, bromides or iodides. The iodides and bromides are preferred.

The conversion into an alkali metal salt can be carried out in a manner known per se; for example, by reacting the alcohol with an appropriate strong base such as the corresponding alkali metal (e.g., sodium), an alkali metal hydride (e.g., sodium hydride) or an alkali metal amide (e.g., sodium amide).

The reaction of a thus-obtained alkali metal salt with the alkylation or alkenylation agent is preferably carried out in an aprotic organic solvent. Examples of such solvents are hydrocarbons (e.g., benzene or toluene) as well as ethers (e.g., dioxan or tetrahydrofuran). The etherification is expediently carried out at an elevated temperature; for example, above about room temperature, preferably at temperatures between about 70° C and 140° C.

The octadiene derivatives of formula I possess particular odorant properties. They can accordingly be used in the perfume industry for the manufacture of perfumes and perfume products; for example, for the perfuming of soaps, solid and liquid detergents, aerosols and cosmetic products of all kinds such as toilet waters, ointments, face milks, make-ups, lipsticks, bath salts and bath oils. In the finished perfumes or perfumed products, the content of the present octadiene derivatives can lie within wide limits; for example, between about 1% (detergents) and about 20% (alcoholic solutions). In perfume bases or concentrates, the octadiene derivatives can, of course, also be present in amounts greater than 20%.

The octadiene derivatives provided by the present invention provide, in general, a flowery, especially lavender-like, odor without a fatty note. The free alcohol, namely the octadiene derivative of formula I in which R represents a hydrogen atom, possesses outstanding fragrance qualities, the odor thereof being pleasantly flowery (reminiscent of lavender), linalool-like, piquant, earthy, slightly metallic and long-lasting. The compositions which contain this alcohol have a powerful, fresh action; the alcohol being especially suitable for flowery, woody or hesperidine notes.

The octadiene derivative of formula I in which R represents an acetyl group possesses a natural flowery, fruity, green, slightly woody odor which is somewhat reminiscent of grapefruit and neroli and which is vetiver-like in the background. Compositions containing this octadiene derivative accordingly have a very natural action.

The ethers of formula I, especially the methyl ether, are readily volatile compounds and they can accordingly be used in perfume compositions, especially for head-notes.

The octadiene derivatives of formula I can be advantageously incorporated into odorant compositions of the flowery type. Such compositions thereby acquire strength and cohesion and are thus modified in an advantageous manner.

It will accordingly be appreciated that the invention includes within its scope (a) an odorant composition which contains as an essential odor-imparting ingredient an octadiene derivative of formula I and (b) a method of imparting an odor to materials which comprises applying to said materials or incorporating therein an octadiene derivative of formula I hereinbefore or an odorant composition as hereinbefore defined.

The following Examples illustrate the process provided by the present invention:

EXAMPLE 1

44 g of a mixture containing 68% of 2,7-dimethyl-1,3,7-octatriene together with cyclic 6-ring dimers of isoprene (obtained by the selective dimerization of isoprene by the action of palladium salts), 0.5 g of 2,6-di(-tertbutyl)-4-methylphenol and 43 g of liquid sulphur dioxide are stirred for 2 hours at 80° C in a 300 ml stainless steel autoclave. The pressure thereby rises to 10 atmospheres. After cooling, the excess sulphur dioxide is evaporated. The residue is freed from unreacted compounds by distillation up to a flask temperature of 70° C/5 Torr. There are obtained 41.6 g of residue, corresponding to a yield of 94% of theory of crude sulphone of formula III, 4-methyl-2-(3-methyl-3-butenyl)-2,5-dihydro-thiophene-1,1-dioxide, calculated on the pure triene starting material used. Distillation gives a yellow oil of boiling point 80° C/0.03 mm Hg; $n_D^{20} = 1.5120$; $d_4^{20} = 0.9543$.

41.6 g of the crude sulphone of formula III are mixed with 125 g of 50% sulphuric acid at 20° C in a three-necked flask provided with a stirrer and thermometer. The mixture is stirred vigorously for 30 minutes at 20° C, then poured into 350 ml of ice-cold water. The mixture is neutralized at 30° C with 30% sodium hydroxide to a pH of 8. The aqueous solution is extracted three times with 200 ml of benzene each time and the benzene layers are combined. After evaporation of the benzene, there are obtained 39.1 g of a residue corresponding to a yield of 86% of theory of the crude sulphone hydrate of formula IV, 4-methyl-2-(3-methyl-3-hydroxybutyl)-2,5-dihydrothiophene-1,1-dioxide. Distillation gives a yellow oil.

39.1 g of the crude sulphone hydrate of formula IV are distilled at 3 Torr at an oil-bath temperature of 150° C through a short Vigreux column in the presence of 0.5 g of 2,6-di(tertbutyl)-4-methylphenol and 0.5 g of calcium carbonate. By repeated distillation of the distillate there are obtained 16.5 g of pure 2,7-dimethyl-5,7-octadien-2-ol of boiling point 105° C/12 mm Hg; $n_D^{20} = 1.4820$; $d_4^{20} = 0.8684$. The yield is 48.5% of theory calculated on the pure triene used.

EXAMPLE 2

6.7 g of 2,7-dimethyl-5,7-octadien-2-ol, 13 g of isopropenyl acetate and 0.1 g of p-toluenesulphonic acid are heated at reflux for 3 hours in a three-necked flask provided with a thermometer, stirrer and reflux condenser. The mixture is taken up in 100 ml of hexane and washed with a saturated sodium bicarbonate solution and with water. The solvent is distilled off and the residue fractionally distilled. There are obtained 3.4 g of 2,7-dimethyl-5,7-octadien-2-ol acetate of boiling point 60°

C/0.2 mm Hg; $n_D^{20} = 1.4675$; $d_4^{20} = 0.9077$. The yield is 40% of theory.

EXAMPLE 3

4.8 g (0.11 mol) of a 50% suspension of sodium hydride in paraffin oil are mixed with 120 ml of benzene in a three-necked flask provided with a thermometer, stirrer, reflux condenser and dropping funnel. 16.9 g of 2,7-dimethyl-5,7-octadien-2-ol are slowly added dropwise thereto. The reaction is completed by heating the mixture at reflux for 2 hours. 28 g (0.2 mol) of methyl iodide are then added dropwise at 30° C. After completion of the addition, the mixture is heated at reflux for 2 hours. After cooling, 50 ml of water are cautiously added. The benzene layer is separated and washed neutral with water. The solvent is distilled off and the residue fractionally distilled. There are obtained 13.7 g of 2-methoxy-2,7-dimethyl-5,7-octadiene of boiling point 72° C/3 mm Hg; $n_D^{20} = 1.4670$; IR n° 24872 (s 1085 cm$^{-1}$); NMR n° 23421 (3.17 ppm, 3 H, S, —O—CH$_3$). Odor: natural, fresh, reminiscent of lavender; suitable in combination with esters.

EXAMPLE 4

By carrying out the procedure described in Example 3 using allyl bromide in place of methyl iodide there is obtained 2-allyloxy-2,7-dimethyl-5,7-octadiene of boiling point 92°–93° C/3 mm Hg; $n_D = 1.4740$. Odor: lavender-like, fruity.

The following Example illustrates typical odorant compositions containing the octadiene derivatives provided by the present invention:

Example A

| a) Compositon (Rose) | Parts by weight |
| --- | --- |
| 2,7-Dimethyl-5,7-octadien-2-ol | 100 |
| C$_{10}$-Aldehyde 10% in diethylphthalate | 2 |
| C$_8$-Aldehyde 10% in diethylphthalate | 3 |
| C$_9$-Aldehyde 10% in diethylphthalate | 5 |
| Guayl acetate | 10 |
| Phenylethyl acetate | 15 |
| Benzyl acetate | |
| Methylionone (Isoraldeine 70) | 20 |
| Phenylacetaldehyde (10% in diethyleneglycol monoethyl ether) | 20 |
| Dimethylbenzyl carbinyl acetate | 20 |
| Rosacetol | 25 |
| Eugenol | 30 |
| Nerol | 50 |
| Geraniol | 80 |
| Citronellol | 100 |
| Rhodinol pure | 120 |
| Phenylethylalcohol extra | 180 |
| Total | 800 |

| b) Composition (Gardenia) | Parts by weight |
| --- | --- |
| 2,7-Dimethyl-5,7-octadien-2-ol-acetate | 130 |
| Isoeugenol | 5 |
| C$_{14}$-Aldehyde 10% in diethylphthalate | 10 |
| Musk ambrette | 10 |
| Gardenol | 10 |
| Methyl benzoate | 20 |
| Benzyl acetate | 20 |
| Musk ketone | 20 |
| Nonalactone 10% in diethylphthalate | 30 |
| Ylang Ylang extra | 30 |
| Hydroxycitronellal | 35 |
| Dimethylbenzyl carbinyl acetate | 50 |
| Phenylethylalcohol extra | 80 |
| α-Ionone | 100 |
| Hexylcinnamic aldehyde | 100 |
| Total | 650 |

| c) Composition | Parts by weight |
| --- | --- |
| 2-Methoxy-2,7-dimethyl-5,7-octadiene | 120 |
| Rhodinol 70 (rhodinol: citronellol = 70:30) | 80 |
| Vetiveryl acetate | 80 |
| Coumarin | 30 |
| Ylang Ylang bourbon | 30 |
| Sandalwood oil East Indian | 20 |
| Cinnamic alcohol | 10 |
| Nerol | 10 |
| Musk ketone | 50 |
| Musk ambrette | 50 |
| Hydroxycitronellal | 30 |
| Lilial (p-tertbutyl-α-methylhydrocinnamaldehyde | 30 |
| Juniperberry oil | 20 |
| Amber (artificial) | 30 |
| Civet abs. 10% in phthalic acid diethyl ester | 5 |
| Undecalactone 10% in phthalic acid diethyl ester | 5 |
| C$_9$-Aldehyde 1% in phthalic acid diethyl ester | 10 |
| C$_{11}$-Aldehyde 1% in phthalic acid diethyl ester | 10 |
| Cassia abs. 10% in phthalic acid diethyl ester | 80 |
| p-Tertbutylcyclohexyl acetate | 100 |
| Jasmin abs. synth. | 200 |
| Total | 1000 |

The flowery composition can be used for the perfuming of lotions. The ether provided by the present invention conveys thereto a fruity-sweet odor and, in addition, a fine, flowery note.

What we claim is:

1. 2,7-Dimethyl-5,7-octadien-2-ol.

* * * * *